United States Patent
Gemmeke et al.

(10) Patent No.: US 10,758,208 B2
(45) Date of Patent: Sep. 1, 2020

(54) DEVICE FOR ULTRASOUND-SUPPORTED REFLECTION AND TRANSMISSION TOMOGRAPHY

(71) Applicant: KARLSRUHER INSTITUT FUER TECHNOLOGIE, Karlsruhe (DE)

(72) Inventors: Hartmut Gemmeke, Stutensee (DE); Michael Zapf, Karlsruhe (DE); Torsten Hopp, Speyer (DE); Robin Dapp, Gondelsheim (DE); Nicole Ruiter, Durmersheim (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 480 days.

(21) Appl. No.: 15/118,896

(22) PCT Filed: Feb. 19, 2015

(86) PCT No.: PCT/EP2015/000369
§ 371 (c)(1),
(2) Date: Aug. 15, 2016

(87) PCT Pub. No.: WO2015/124301
PCT Pub. Date: Aug. 27, 2015

(65) Prior Publication Data
US 2017/0027544 A1  Feb. 2, 2017

(30) Foreign Application Priority Data

Feb. 20, 2014  (DE) .................. 10 2014 102 157

(51) Int. Cl.
*A61B 8/00* (2006.01)
*A61B 8/08* (2006.01)
(Continued)

(52) U.S. Cl.
CPC .......... *A61B 8/4477* (2013.01); *A61B 8/0825* (2013.01); *A61B 8/14* (2013.01);
(Continued)

(58) Field of Classification Search
CPC ....... A61B 8/4477; A61B 8/0825; A61B 8/14; A61B 8/15; A61B 8/4494
See application file for complete search history.

(56) References Cited

U.S. PATENT DOCUMENTS

| 4,279,157 A | 7/1981 | Schomberg et al. |
| 4,478,083 A | 10/1984 | Hassler et al. |

(Continued)

FOREIGN PATENT DOCUMENTS

| DE | 2827423 A1 | 1/1980 |
| DE | 10050232 A1 | 5/2005 |
| EP | 2056124 A1 | 5/2009 |

OTHER PUBLICATIONS

N. V. Ruiter et al: "First results of a clinical study with 3D ultrasound computer tomography", 2013 IEEE International Ultrasonics Symposium (IUS), Jul. 2, 2013 (Jul. 2, 2013), pp. 651-654, XP055191862.

(Continued)

*Primary Examiner* — Bill Thomson
*Assistant Examiner* — Aminah Asghar
(74) *Attorney, Agent, or Firm* — Leydig, Voit & Mayer, Ltd.

(57) ABSTRACT

A device for ultrasound-assisted reflection and transmission tomography includes a measurement volume filled with an ultrasonic coupling medium and having an opening for inserting a body to be examined and a lateral surface remote from the opening, and a number of ultrasonic transducers arranged remotely from the opening of the measurement volume, arranged in direct contact with the ultrasonic cou- (Continued)

pling medium, and arranged oriented into the measurement volume. The arrangement of the ultrasonic transducers around the measurement volume aperiodically follows a random uniform distribution.

10 Claims, 9 Drawing Sheets

(51) Int. Cl.
*A61B 8/14* (2006.01)
*A61B 8/15* (2006.01)

(52) U.S. Cl.
CPC .............. *A61B 8/15* (2013.01); *A61B 8/4494* (2013.01); *A61B 8/406* (2013.01); *A61B 8/42* (2013.01)

(56) References Cited

U.S. PATENT DOCUMENTS

| | | |
|---|---|---|
| 5,673,697 A | 10/1997 | Bryan et al. |
| 6,488,630 B1* | 12/2002 | Hand ........................ A61N 7/02 600/459 |
| 2003/0158481 A1 | 8/2003 | Stotzka et al. |
| 2005/0203370 A1* | 9/2005 | Patch ..................... A61B 5/0095 600/407 |
| 2008/0319318 A1* | 12/2008 | Johnson ................ A61B 8/0825 600/445 |
| 2009/0230823 A1 | 9/2009 | Kushculey et al. |
| 2011/0021923 A1* | 1/2011 | Daft ..................... G01S 15/8925 600/459 |
| 2011/0130663 A1* | 6/2011 | Raju ........................ A61N 7/00 600/459 |
| 2016/0022490 A1* | 1/2016 | Ergun ...................... A61B 8/10 600/439 |

OTHER PUBLICATIONS

Diarra Bakary et al: "Design of Optimal 2-D Nongrid Sparse Arrays for Medical Ultrasound", IEEE Transactions on Biomedical Engineering, IEEE Service Center, Piscataway, NJ, USA, vol. 60, No. 11, Nov. 2, 2013 (Nov. 2, 2013), pp. 3093-3102, XP011529522.

* cited by examiner

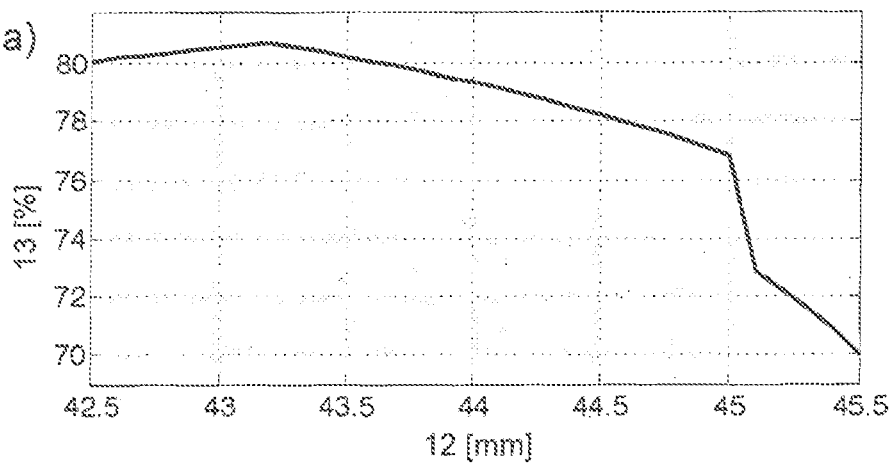
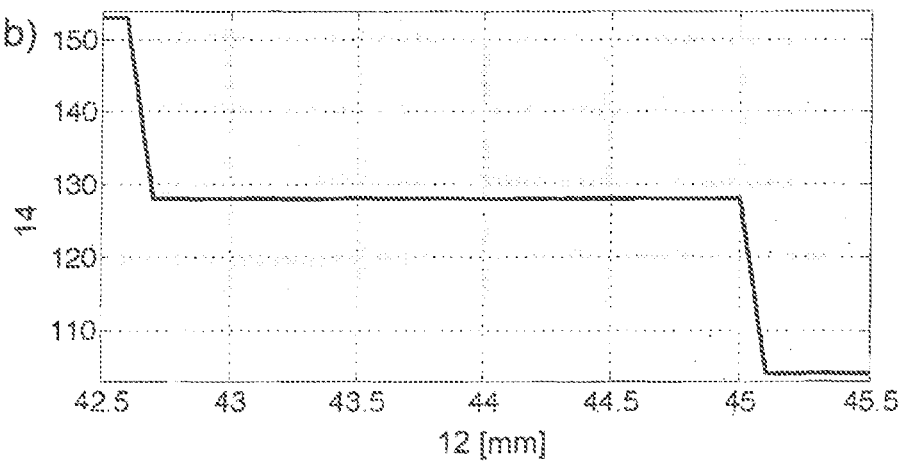
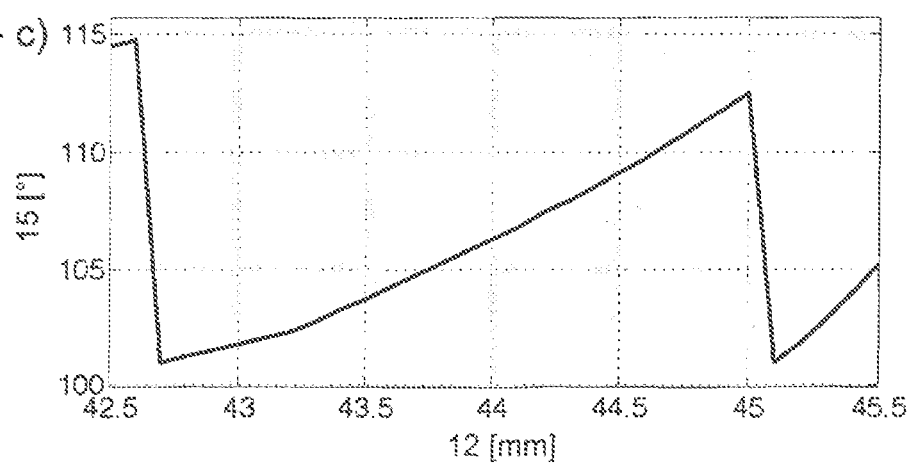

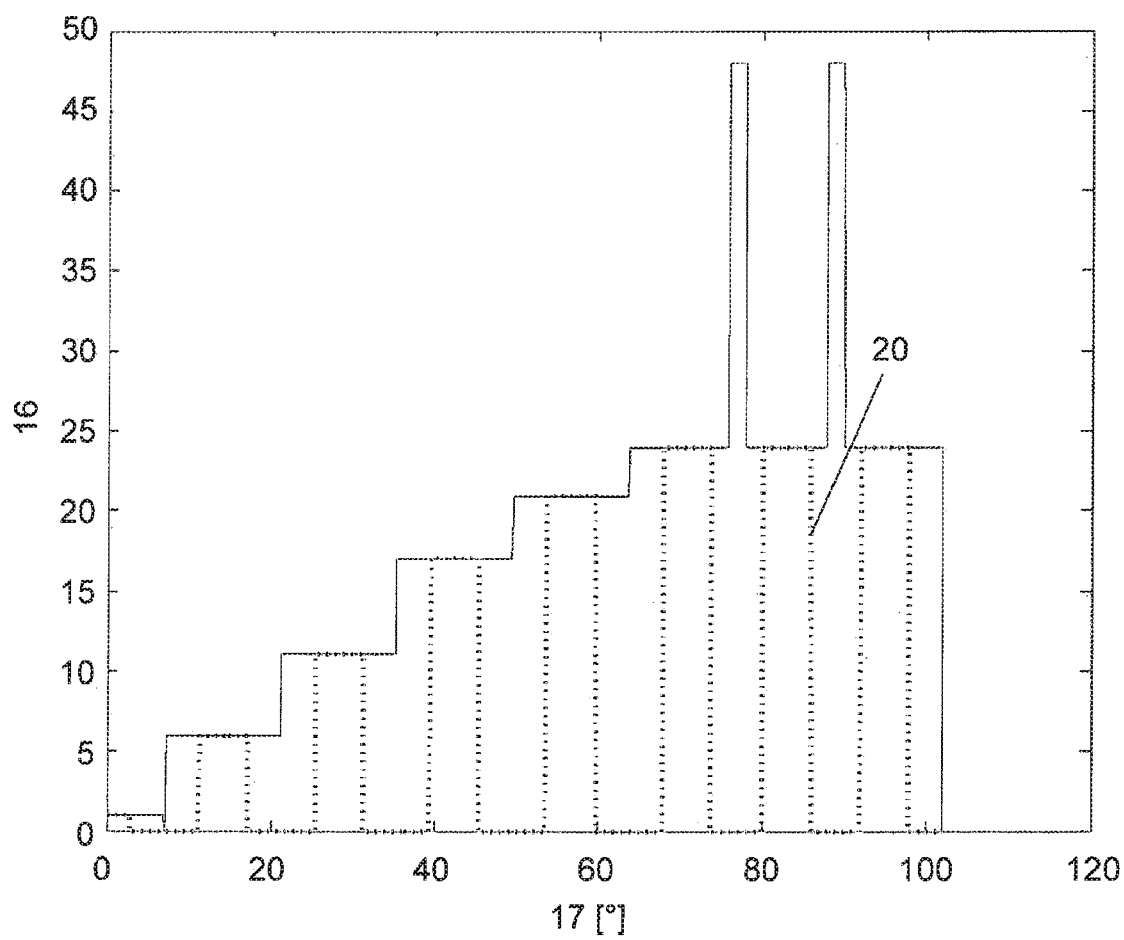

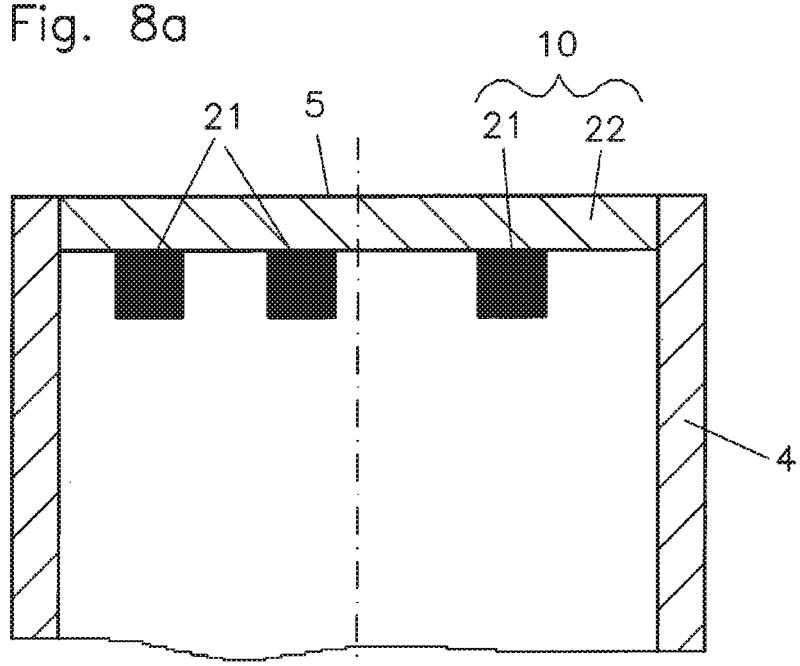
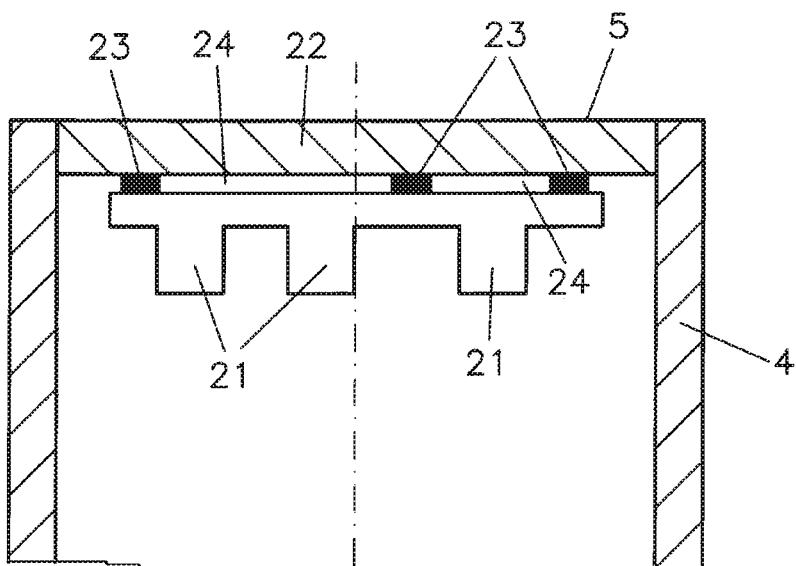

DEVICE FOR ULTRASOUND-SUPPORTED REFLECTION AND TRANSMISSION TOMOGRAPHY

CROSS REFERENCE TO RELATED APPLICATIONS

This application is a U.S. National Phase application under 35 U.S.C. § 371 of International Application No. PCT/EP2015/000369, filed on Feb. 19, 2015, and claims benefit to German Patent Application No. DE 10 2014 102 157.6, filed Feb. 20, 2014. The international application was published in German on Aug. 27, 2015 as WO 2015/124301 A1 under PCT Article 21(2).

FIELD

The invention relates to a device for reflection and transmission tomography using ultrasound for objects to be examined, in particular for tissue examinations of extremities, in particular of the female breast.

BACKGROUND

Ultrasound-assisted tomography systems of the type mentioned at the outset comprise an arrangement of ultrasonic transducers which are arranged around the object to be examined and the main radiation direction of which is directed towards the object.

DE 28 27 423 A1 describes a device for ascertaining the internal structure of a body using sonic beams, in which the body is introduced into a container filled with a coupling medium and is investigated using ultrasound in said container using the ultrasonic transmission process. Here, the ultrasonic transducers are arranged cylindrically in the container in a matrix.

Likewise, U.S. Pat. Nos. 5,673,697 and 4,478,083 disclose ultrasonic test systems for three-dimensional tomographic imaging of objects, in which systems the ultrasonic transducers are arranged in a matrix shape around a measurement volume.

DE 100 50 232 A1 describes, by way of example, a high-resolution ultrasonic tomograph, in particular for medical examinations, in which a body part to be examined, in particular a female breast, protrudes from above into an ultrasonic coupling medium in an open container. The container wall comprises securely arranged ultrasonic transducers oriented towards the interior of the container over the entire wall surface. Said transducers are controlled as transmitters or receivers either individually or in groups by means of a computer-assisted control and evaluation unit, the ultrasonic signals emitted by the transmitters being ultrasonic pulses. These are conducted to the body part to be examined, are manipulated at this point and are received in parallel by all the receivers in the form of reflection and transmission signals.

In general, when configuring ultrasound-assisted reflection and transmission tomography, the aim is to achieve the highest possible resolution by means of the densest possible distribution of cylindrical ultrasonic measurement heads over the surface of a hemisphere or, more generally, of a rotationally symmetrical half-ellipsoid around the object to be examined. In this case, due to the densest possible arrangement of the ultrasonic transducers, which are as similar as possible, the aim in principle is to position said transducers in a pattern or periodic arrangement relative to one another.

SUMMARY

In an embodiment, the present invention provides a device for ultrasound-assisted reflection and transmission tomography including a measurement volume filled with an ultrasonic coupling medium and comprising an opening for inserting a body to be examined and a lateral surface remote from the opening, and a number of ultrasonic transducers arranged remotely around the opening of the measurement volume, arranged in direct contact with the ultrasonic coupling medium, and arranged oriented into the measurement volume. An arrangement of the ultrasonic transducers around the measurement volume aperiodically follows a random uniform distribution.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIGS. 4a to 4c are each graphs of the maximum achievable relative surface covering (FIG. 4a), the maximum number of sensors (FIG. 4b), and the maximum angle $\theta$ (FIG. 4c) as a function of the diameter of the sensor for an embodiment according to FIG. 1a having a radius of 175 mm;

FIG. 5 is a graph of the distribution of the angle $\theta$ as a function of the angle $\theta$ for the embodiment in FIG. 4;

FIG. 2a) and in an aperiodically randomly uniformly distributed arrangement of ultrasonic transducers (FIG. 7b; cf. FIG. 2b); and FIGS. 8a and 8b are each sections through a preferred embodiment of a transducer field of a transducer element comprising ultrasonic transducers having a shared out-coupling layer.

DETAILED DESCRIPTION

Figure 1A:
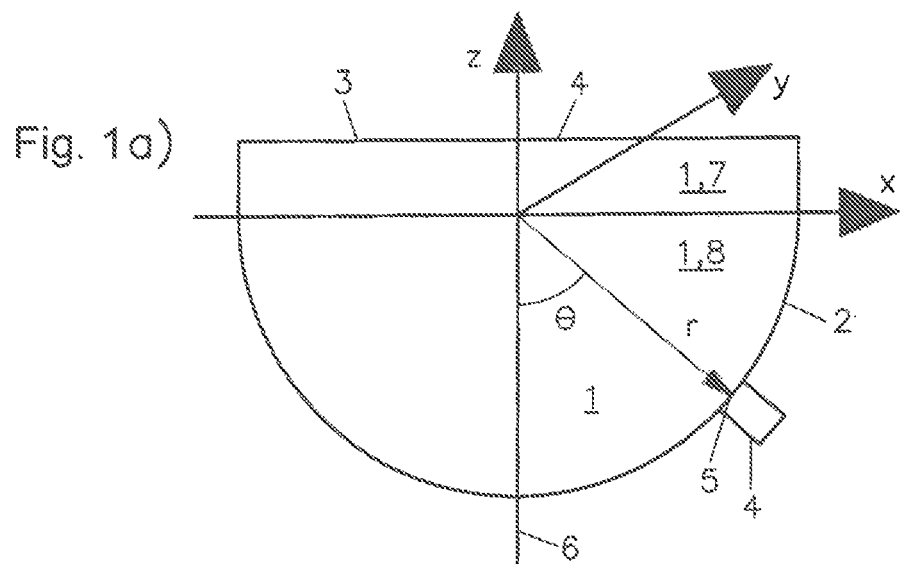
FIGS. 1a to 1d are schematic views of a device according to an embodiment of the invention.

Embodiments of the invention provide an improved image quality, in particular an improved image contrast and a reduction in image artifacts. In particular, a device according to an embodiment of the invention complies with the requirements for cost-effective production.

An embodiment of the invention provides a device for ultrasound-assisted reflection and transmission tomography, comprising a measurement volume filled with an ultrasonic coupling medium, comprising an opening for inserting a body to be examined, such as a body part, for example a female breast or another extremity of the human body. The measurement volume is arranged in a container.

A total number of ultrasonic transducers are arranged around the measurement volume which are in direct contact with the ultrasonic coupling medium, are arranged so as to be remote from the opening around the measurement volume, and are oriented into the measurement volume. An ultrasonic transducer preferably comprises an oscillating element and a coupling means to the surroundings, preferably a piezoelectric oscillating body comprising an out-coupling layer in the sound radiation direction.

The measurement volume is defined by a lateral surface on the side remote from the opening, which is preferably at the top, which surface is either formed by a non-material, imaginary plane, or preferably by a wall, preferably a container wall. The ultrasonic transducers are preferably arranged on this lateral surface, more preferably such that the out-coupling layers of the ultrasonic transducers lie on the lateral-surface plane or are tangential thereto. The ultrasonic transducers are oriented into the measurement volume. The lateral surface is preferably rotationally symmetrical or spherical, and is more preferably formed by a hemisphere or a half-ellipsoid.

In order to operate the device, as described at the outset, the ultrasonic transducers are preferably controlled as transmitters or receivers, preferably individually, by means of a computer-assisted control and evaluation unit. The ultrasonic signals emitted by the transmitters are ultrasonic pulses. A preferred operational configuration provides that the transducers are used both as transmitters and receivers, the transmitters being switched to be a receiver after an ultrasonic signal has been emitted, i.e. made capable of receiving the emitted ultrasonic signal. The device is therefore an essential component of an ultrasonic tomograph.

A notable feature is the arrangement of the ultrasonic transducers around the measurement volume, which arrangement aperiodically follows a random uniform distribution. This also means that any position around the measurement volume in the arrangement described has the same probability of being occupied by an ultrasonic transducer. For this purpose, a total number of preferably at least 1000, more preferably at least 2000 and at most 10,000, even more preferably 5000, 3000 or 2500, ultrasonic transducers are provided. Owing to the randomly uniformly distributed arrangement, the ultrasonic transducers are at distances from directly adjacently arranged ultrasonic transducers that do not have any distinct maximums, but are likewise uniformly distributed in a value interval for the distances. Using the example of a device for ultrasound mammography, said distances are preferably in the value ranges of between 1 and 30 mm, preferably of between 2 and 10 mm and more preferably of between 3 and 8 mm. In order to ensure that the distribution is random, the distances between the ultrasonic transducers should be spread over a wide region.

Owing to the aperiodically random uniform distribution of the distances between respectively directly adjacent ultrasonic transducers, the probability of radiation maximums and minimums for the ultrasonic signals is reduced. During reconstruction, the loci (ellipses) therefore only statistically become more frequent. The invention therefore increases the contrast at least by a factor of 6 compared with the arrangement described in DE 100 50 232 A1. In an aperiodically random uniform distribution, the ultrasonic transducers do not however have a periodic arrangement or identical distances from one another. Periodic suppression or addition of signals by superposition therefore no longer takes place at particular radiations angles relative to all the transducers, but takes place individually for each transmission transducer distance. Periodic disturbance variables, such as these radiation maximums and minimums (grating lobes), are distributed by an equally aperiodically random uniform distribution of the arrangement of the transducers, and this reduces the bandwidth of these disturbance variables and allows essentially improved isolation of useful signals and disturbance variables and thus allows improved image quality and improved contrast. In particular, these disturbance variables are no longer added to separate maximums and minimums at particular angles, but instead are spread over the entire angular range and approximate a continuous curve for an average value in the total of their frequency of occurrence.

All the ultrasonic transducers are oriented into the measurement volume, i.e. their out-coupling layers point towards the measurement volume and are in direct contact with the ultrasound coupling medium, preferably a liquid, preferably an aqueous solution or an ultrasound coupling gel.

In the context of a first embodiment, the respective main radiation directions of the ultrasonic transducers are oriented orthogonally into the measurement volume. An alternative embodiment provides that the main radiation directions are not orthogonal, i.e. for a spherical lateral surface are oriented towards the center of the sphere, but are oriented in different directions, preferably so as to be randomly uniformly distributed. Therefore, the ultrasonic energy input into the measurement volume is not focused on one point, namely the center of the sphere, but is distributed uniformly into the measurement volume or a central part thereof (e.g. towards the volume of the body to be examined in the measurement volume).

In a particularly preferred embodiment, the ultrasonic transducers which are arranged so as to be aperiodically randomly uniformly distributed around the measurement volume, preferably on the lateral surface, are divided over a plurality of transducer fields, the arrangements of the ultrasonic transducers over each transducer field following an aperiodically random uniform distribution. Here, it is also advantageous for the ultrasonic transducers not to be arranged in a rotationally symmetrical pattern. Each transducer field contains a group of ultrasonic transducers. Preferably, the ultrasonic transducers in a transducer field share an out-coupling layer, which extends over the oscillating elements of all the ultrasonic transducers in the transducer field.

The ultrasonic transducers and thus the transducer fields are preferably arranged on the lateral surface, around the measurement volume. In this case, the transducer fields are arranged side by side, i.e. they do not overlap one another. The highest possible surface coverage is sought, i.e. a dense arrangement of transducer fields on the preferably spherical lateral surface, which is why respectively adjacent transducer fields are arranged side by side as far as geometrically possible, until they are touching. In principle, the transducer fields are round, ellipsoid, oval or polygonal. Polygonal transducer fields have at least three corners, the lengths of the edges preferably being equal.

The highest possible surface coverage is achieved by transducer fields of different shapes and sizes, for example having first transducer-field fractions that are arranged as close to one another geometrically as possible, as mentioned above, with geometrically smaller second and optionally further transducer-field fractions being inserted in the spaces arising in this arrangement. For example, in a possible embodiment, a first transducer fraction is pentagonal and a second transducer fraction is hexagonal, in the manner of a football.

Preferably, however, the transducer fields are geometrically identical, i.e. the size and shape thereof is identical. An arrangement of the ultrasonic transducers which is identical in every transducer field is particularly advantageous for cost-effective production. The transducer fields and thus the sensors therefore all have the same (aperiodically randomly uniformly distributed) arrangement having non-rotationally symmetrical arrangement patterns of the ultrasonic transducers and can therefore be produced in series more easily. In order to prevent periodicity when identical sensors are linked together, said sensors, and thus the transducer fields having the arrangement patterns of the ultrasonic transducers, are used so as to be rotated relative to one another, preferably by an individual random degree of rotation.

A particularly preferred embodiment provides a circular design of the transducer fields, which provides the advantage of continuous and thus uniformly distributable rotation of the transducer fields relative to one another. Owing to this uniformly distributable rotation together with the maximum possible degrees of freedom of the adjustability of the rotational angle for the rotation, it is possible to further ensure against randomly occurring periodic arrangements by adjacent transducer fields by contrast with polygonal transducer fields (number of corners usually corresponds to the number of adjustable rotational angles).

The random uniform distribution of the ultrasonic transducers on the lateral surface is produced, using the above-mentioned concept, locally on the transducer field and furthermore by random rotation and by packing the transducer fields as densely as possible on the lateral surface. Using the above-mentioned distribution of the ultrasound transducers, in one position of the measuring arrangement, $5 \cdot 10^6$ measuring spectra (A scans) can be recorded when all the transducer positions are used simultaneously to transmit and receive. This is sufficient to produce a complete 3D image in the device. Conventional systems require at least six rotational and lifting positions of the measuring arrangement for this purpose in order to achieve sufficient image quality. By comparison, a contrast that is higher by at least a factor of 6 can be achieved in reflection tomography, and image quality that is improved by a factor of 2 can be achieved in transmission tomography. This means a shorter data acquisition time in the range of a few minutes, in which the mechanical movements of the measurement arrangement can also be reduced to 1-3.

The embodiments shown in FIGS. 1a to 1d show possible embodiments of the measurement volume 1 which each have lateral surfaces 2 and an opening 3 at the top, which preferably extend rotationally symmetrically about an axis of symmetry 6. The lateral surfaces are preferably designed as a vessel wall and a retaining structure for the transducer elements 4, their transducer surfaces 5 having the ultrasonic transducers inserted therein preferably being arranged in a planar manner on the lateral surface. The measurement volumes shown have cylindrical portions 7 and/or spherical portions 8 and/or ellipsoid portions 9. A cylindrical portion is distinguished as being different from the spherical and ellipsoid portions, preferably by means of ultrasonic transducers that are directed directly towards one another in one plane, and is suitable in particular for ultrasound transmission tomography. By contrast, spherical and ellipsoid portions are suitable in particular for covering larger ranges of the angle θ (cf. FIGS. 5, 7a and 7b) and thus for reflection and scattering tomography.

Figure 1B:
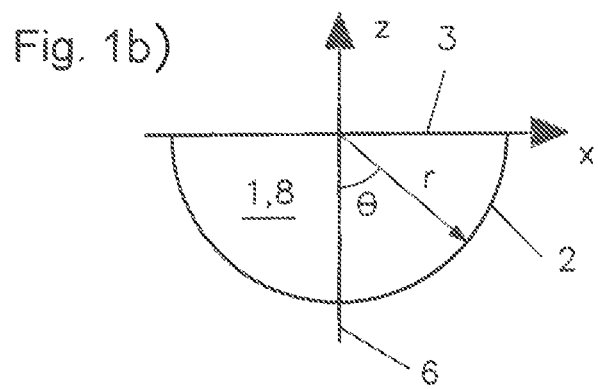

FIG. 1a shows a measurement volume 1 comprising a cylindrical portion 7 and a hemispherical portion 8 having a radius of curvature r, starting from the line of symmetry 6. The embodiment according to FIG. 1b shows an identical spherical portion 8 of the measurement volume 1 that is designed as a hemisphere, but does not have the cylindrical portion.

Figures 1C, 1D:
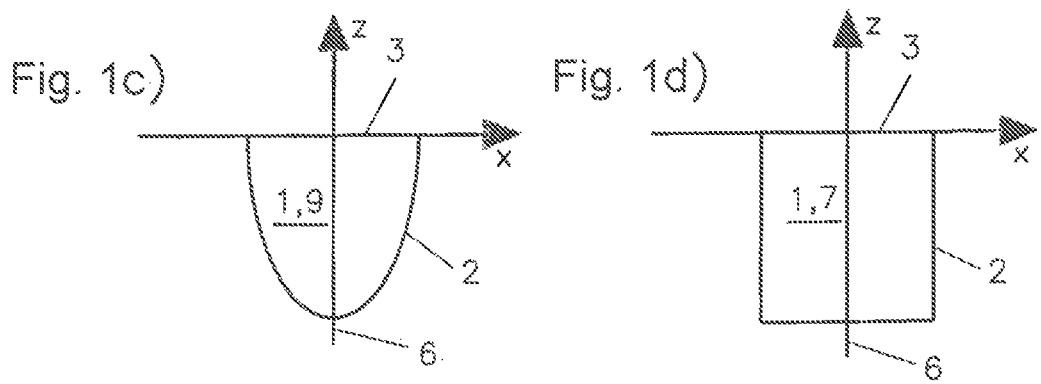

FIG. 1c shows an embodiment comprising a measurement volume having an ellipsoid lateral surface, i.e. exclusively having an ellipsoid portion of the measurement volume 9. Due to the narrower shape of the measurement volume that is preferably rounded in the lower region, the angular range that is advantageous for reflection and scattering tomography is limited. Arrangements comprising ultrasonic transducers having small angles θ are only provided in smaller numbers, while arrangements having the angular ranges with angles θ of around 90±30°, preferably 90±10°, that are advantageous for ultrasound transmission tomography cover larger regions of the lateral surface. Furthermore, this embodiment can also be combined with a cylindrical portion (not specifically shown) in the region of the opening (similar to FIG. 1a).

Lastly, FIG. 1d shows a measurement volume having an exclusively cylindrical portion 7 specifically for transmission tomography.

Other configurations (not shown in the drawings) of a measurement volume that is rotationally symmetrical about the line of symmetry provide an angular approximation of the above-mentioned cross sections of the measurement volume, for example comprising a cylindrical portion 7, to which one or more frustoconical portions are joined instead of the spherical portion 8 shown in FIG. 1a, and which converge at a point in the lower region, or preferably end in a planar circular area.

Figure 2A:
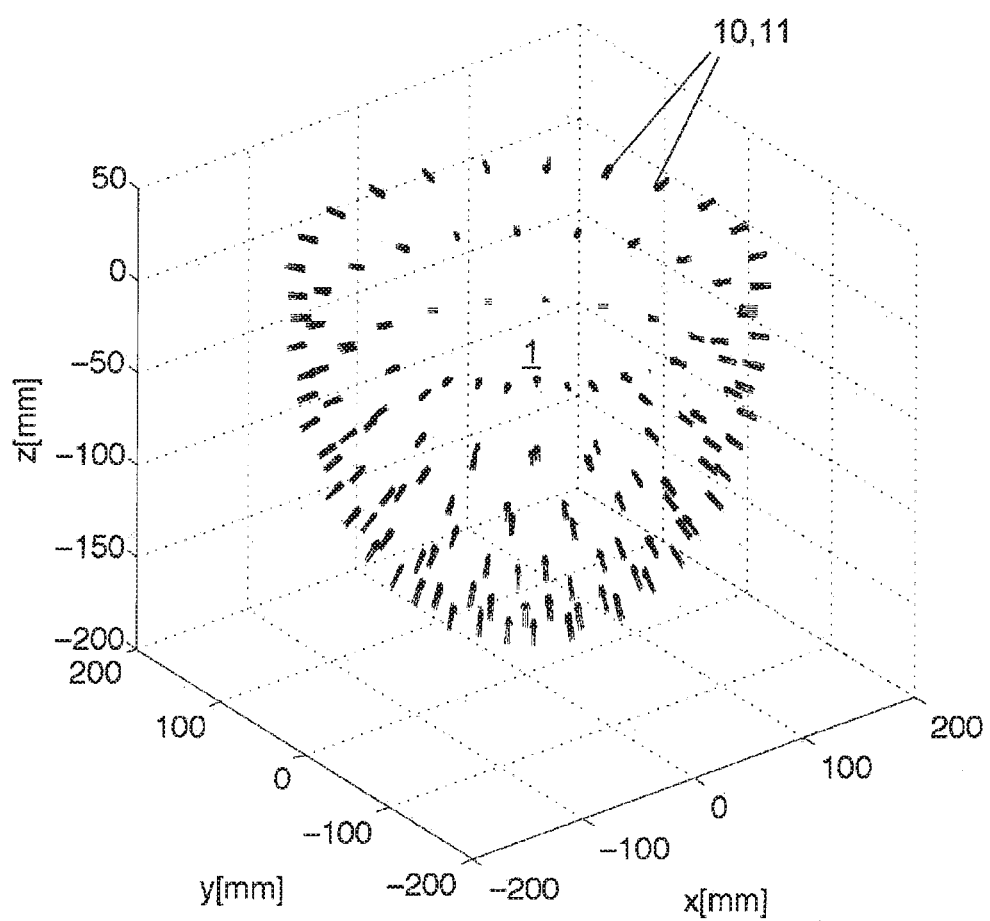
FIGS. 2a and 2b are each three-dimensional views of ultrasonic transducers around a measurement volume.
Figure 2B:
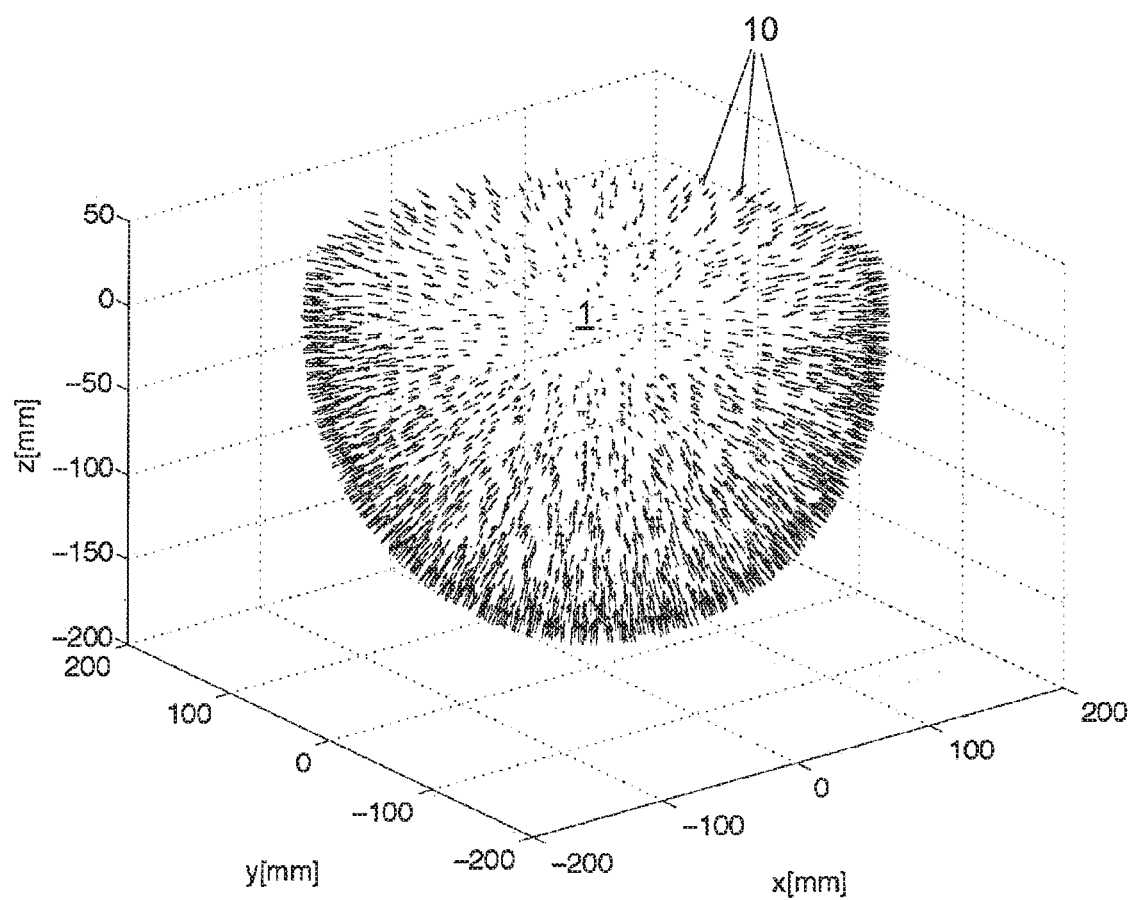

By way of example, FIGS. 2a and 2b are each perspective views of ultrasonic transducers 10 around a measurement volume 1 in a geometry shown in FIG. 1a. The radius of curvature r is for example 175 mm, and the height of the cylindrical portion of the measurement volume is for example 211.5 mm.

FIG. 2a shows grouping of the total of 2028 ultrasonic transducers 10 into ultrasonic-transducer groups 11 in a square arrangement (e.g. 156 ultrasonic-transducer groups each having nine receiver transducers and four transmitter transducers in a square formation with an approximately 5 mm edge length, corresponding to chessboard-pattern-type nesting), which are in turn arranged at equal distances from one another. This periodic arrangement corresponds, locally and as a whole, to that described in the above-mentioned prior art.

By contrast, FIG. 2b shows an arrangement of approximately 2300 ultrasonic transducers which follows an aperiodically random uniform distribution, avoiding periodic distances. The distances between adjacent ultrasonic transducers are for example between 2.4 and 9.2 mm, with the same distribution probability.

Figure 3:
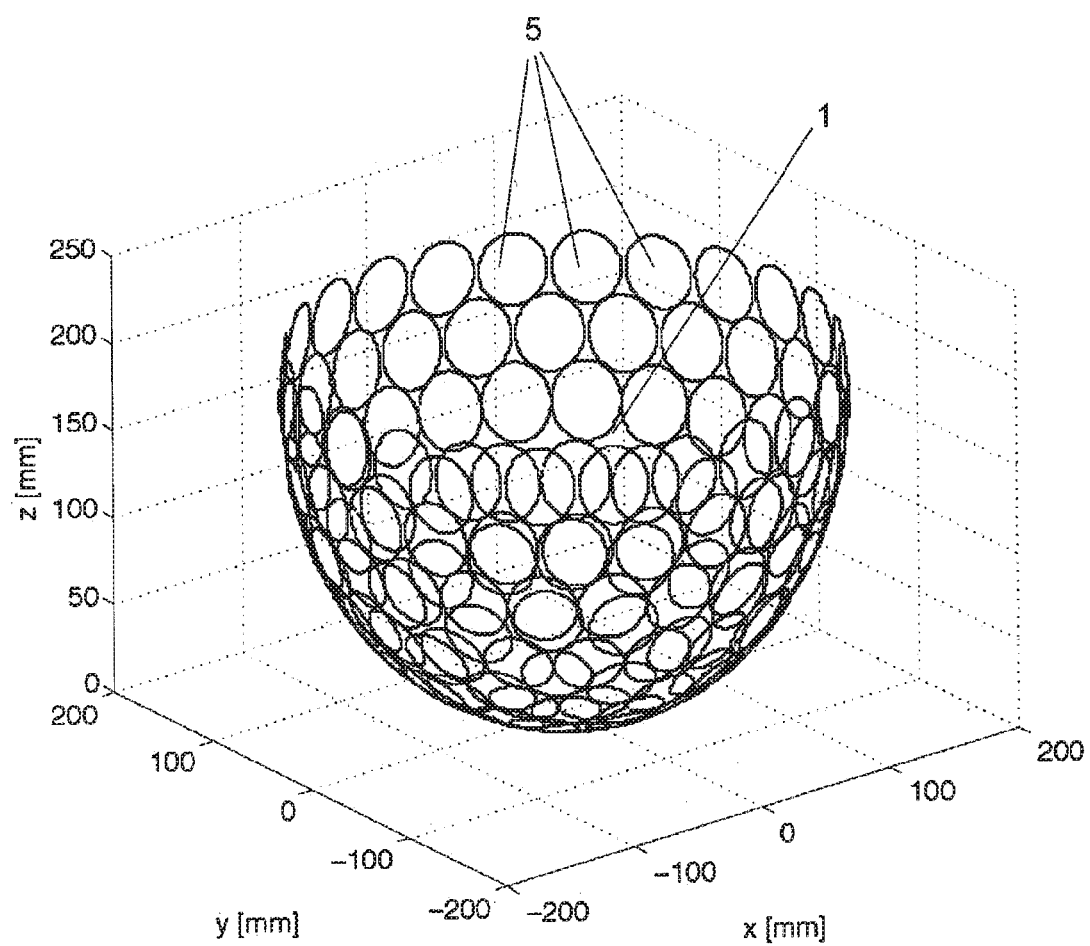
FIG. 3 is a three-dimensional view of circular transducer fields in a preferred dense arrangement around a measurement volume.

Preferably, the uniformly distributed ultrasonic transducers as described above are arranged in transducer fields. FIG. 3 shows, by way of example, the densest possible arrangement of round transducer fields 5 on a lateral surface of the measurement volume 1 (radius of curvature r=175 mm) shown in FIGS. 2a and 2b. Each transducer field is round and has a predefined identical diameter, and each ultrasonic transducer is located in one of the transducer fields in this embodiment. More preferably, all the transducer fields, and in particular their arrangement and number of ultrasonic transducers, are identical, the geometric arrangement of ultrasonic transducers in the transducer fields following an aperiodically random uniform distribution. Periodicity of the transducer fields is prevented by randomly uniformly distributed rotation of adjacent transducer fields.

For the densest possible surface coverage 13 that is sought for the lateral surface shown in FIGS. 1a and 3 by round transducer fields, it is essential to set a defined ratio between the radius of curvature r and the diameter of the transducer fields 12, as can be seen in FIG. 4a. For a radius of curvature r of 175 mm, maximum surface coverage of 80.7% can be achieved using transducer fields having a diameter of 43.2 mm, and this corresponds to a ratio of radius of curvature r to diameter 12 of 4.05. Very high surface coverage of over 80% is for example achieved using transducer-field diameters of between 42.5 mm and 43.6 mm, at which said ratio is calculated at values in the preferred interval of between 4.01 and 4.12. Other starting values for the radius of curvature and the transducer-field diameter lead to identical relative surface coverage if said ratios and thus the proportions relative to one another are maintained. FIG. 4b shows the stepped progression of the number 14 of transducers to be accommodated on the lateral surface as a function of the diameter of the transducer fields 12. The maximum achievable angle θ (shown in FIG. 1a) also changes in a stepped manner together with the steps, and as the number of transducer fields from FIG. 4b increases, the maximum achievable angle 15 also increases (FIG. 4c).

Using the example according to FIG. 2b, FIG. 5 shows the distribution of the transducers 16 as a function of the distribution of the angle θ 17 in a histogram (solid line), the region above 70° being high owing to the cylindrical portion of the measurement volume. In the region of the equator, i.e. the differentiably constant transition from the hemisphere to the cylinder, the optimization has accommodated three interlockingly arranged rings that each contain 24 transducer fields (cf. FIG. 3). Owing to the wall thickness and the minimal distance of the sensors from the wall of the planar transducer fields according to FIG. 6, the usable region 20 is limited, and specifically to the regions indicated by dotted lines.

Figure 6:
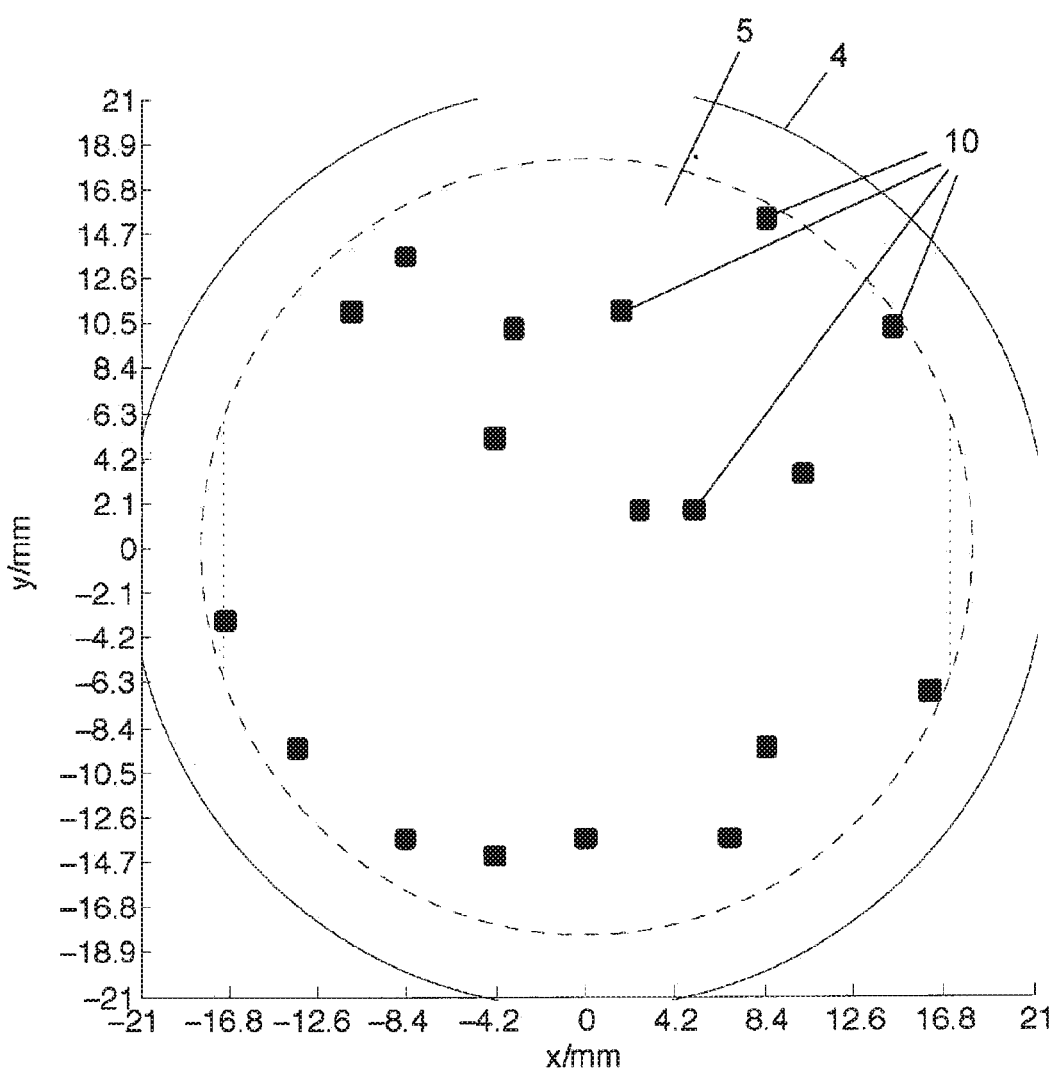
FIG. 6 is a schematic plan view of an exemplary arrangement pattern of ultrasonic transducers that are uniformly distributed aperiodically randomly over a round transducer field.

FIG. 6 shows an exemplary plan view of a round transducer field 5 having a diameter of 43.2 mm and 18 uniformly distributed ultrasonic transducers 10 therein. The preferably planar transducer field forms the edge of a cylindrical transducer element in a tubular housing, the inner wall of which is shown by a dashed line. Preferably, all the ultrasonic transducers have a shared out-coupling layer, which extends over the entire transducer field.

Figure 7:
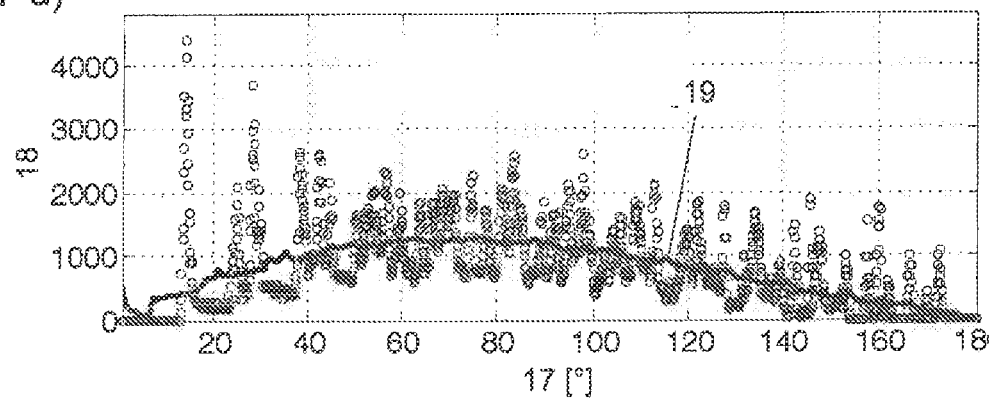
FIGS. 7a and 7b show the distribution of the ultrasonic transducers as a function of the angle $\theta$ in a conventional arrangement of ultrasonic transducers (FIG. 7a; cf.
Figure 7:
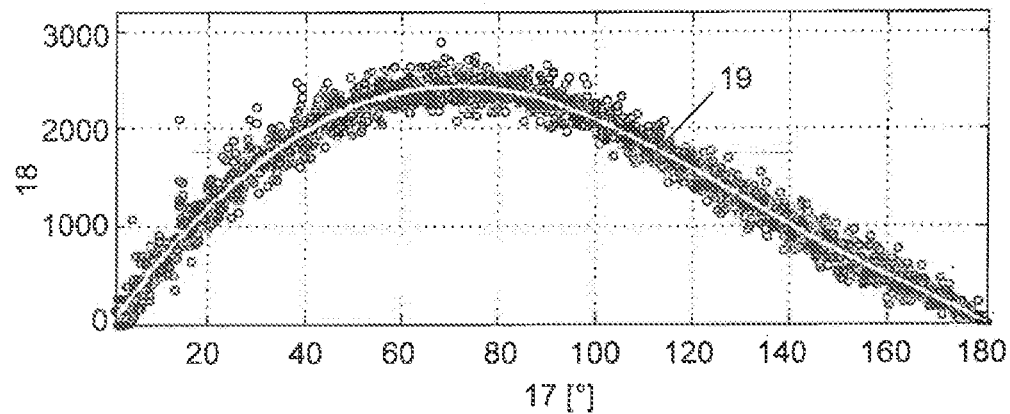

FIGS. 7a and 7b show the distributions of the ultrasonic transducers 18 over the angle θ 17 in a conventional arrangement of ultrasonic transducers (FIG. 7a; cf. FIG. 2a) and in an aperiodically randomly uniformly distributed arrangement of ultrasonic transducers in transducer fields (FIG. 7b), as shown by way of example in FIG. 3b and FIG. 6. The measurement volume and its dimensions correspond to that described in FIGS. 2a and 2b, and in FIG. 3. Without uniform distribution, clear maximums and minimums become apparent that also extend periodically over the entire angular range. The variability in the distribution values around the relevant median-value curve 19 is calculated to be $2.56 \cdot 10^5$ for the conventional arrangement according to FIG. 2a, and reduces to $3.98 \cdot 10^3$ for the uniformly distributed arrangement of the ultrasonic transducers around the measurement volume.

FIGS. 8a and 8b are each sectional views through preferred embodiments of a transducer field 5 of a transducer element 4 comprising ultrasonic transducers having a shared out-coupling layer. Here, an ultrasonic transducer comprises a piezoceramic oscillating element 21 having at least one lower and one upper electrode and an out-coupling means, which is formed by a shared out-coupling layer 22 for all the oscillating elements of the transducer element and covers the entire transducer field 5. In the embodiment described, the out-coupling layer 22 consists of a printed circuit board, preferably in its entirety but at least in part, on which the oscillating elements 21 are each connected to one of their electrodes. Strip-conductor structures having a constant strip-conductor height are provided on the printed circuit boards underneath the piezoelectric oscillating elements and are in electrical contact with an electrode of the oscillating element.

FIG. 8a shows the embodiment in which the oscillating elements comprising an electrode are individually placed onto the conductor strips of the printed circuit board and are connected to known means, for example electrically conducting adhesive, for example in the form of an SMD component. In this case, the conductor strips are used as spacers.

By contrast, FIG. 8b shows an alternative embodiment in which the oscillating elements project in the form of raised portions on a monolithic molded element made of a piezoelectric material and are positioned at a predefined distance from the printed circuit board by means of spacer elements 23 remote from the oscillating elements. The cavity 24 that is left between the printed circuit board and the piezoelectric oscillating element 21 is completely filled with a binder, for example an electrically conductive adhesive, beside the conductor-strip structure.

The printed circuit board and the binder have acoustic impedance, which is between the piezoelectric oscillating bodies and the ultrasound coupling medium in the measurement volume.

An essential basic concept, in particular of the last-mentioned embodiments, is that of positioning and securing the piezoelectric oscillating elements, which comprise one of the two electrode surfaces that are arranged so as to be plane-parallel to one another and are on spacer elements, on a printed circuit board in a simple manner such that they are precisely aligned, electrically contacting, plane-parallel and reproducible. This advantageously facilitates series production of transducer fields equipped with ultrasonic transducers as an essential component of the transducer elements. For this purpose, a conductor-strip structure that has been etched out of a two-dimensional coating on the printed circuit board or applied using a thick-film technique (e.g. by screen printing) is preferably located on the printed circuit board. Said structure is used both to provide electrical contact with the electrode surface and also as a spacer element between the printed circuit board and the piezoelectric oscillating elements, and specifically such that it extends over the entire electrode region. Solders or adhesives which locally penetrate and completely fill the cavities left beside the conductor-strip structure between the printed circuit board and the oscillating element when the piezoelectric oscillating elements and the printed circuit board are pressed together are suitable for securing the piezoelectric body to the printed circuit board. The oscillating elements are attached by being pressed against the conductor-strip structure, the adhesive or the solder being through-contacted at at least one point by the conductor-strip structure and the electrode surface meeting. The conductor-strip structure is therefore used simultaneously as an electrical connection for the radiation-side electrode surface. The thickness of the entire out-coupling system, consisting of the printed circuit board and binder in the cavity, is ideally a quarter of the ultrasonic frequency λ/4 applied to the ultrasonic transducers.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS 1 measurement volume
2 lateral surface
3 opening
4 transducer element
5 transducer field
6 line of symmetry
7 cylindrical portion of the measurement volume
8 spherical portion of the measurement volume
9 ellipsoid portion of the measurement volume
10 ultrasonic transducer
11 ultrasonic transducer group
12 diameter of the transducer field
13 surface coverage
14 number of transducers
15 maximum angle θ
16 distribution of the transducers
17 angle θ
18 distributions of the ultrasonic transducers
19 median-value curve
20 usable region
21 oscillating element
22 out-coupling layer
23 spacer element
24 cavity, filled with binder

The invention claimed is:

1. A device for ultrasound-assisted reflection and transmission tomography, comprising:
a measurement volume filled with an ultrasonic coupling medium and comprising an opening configured to receive a body to be examined and a lateral surface remote from the opening, and
a plurality of circular ultrasonic transducer fields, each having an identical, non-rotationally symmetrical arrangement of a plurality of ultrasonic transducers,
wherein the plurality of ultrasonic transducers of each respective circular ultrasonic transducer field are in direct contact with the ultrasonic coupling medium and oriented into the measurement volume, and
wherein the plurality of ultrasonic transducers of each respective circular ultrasonic transducer field are arranged in an aperiodically random uniform distribution due to distances between adjacent ultrasonic transducers being randomly distributed between a maximum distance and a minimum distance,
wherein each respective circular ultrasonic transducer field has a respective rotation angle, and
wherein each respective rotation angle is randomly selected such that the rotation angles of the plurality of circular ultrasonic transducer fields have a uniform distribution.

2. The device according to claim 1, wherein a total number of ultrasonic transducers in the device exceeds 2000.

3. The device according to claim 1, wherein the lateral surface is rotationally symmetrical or spherical.

4. The device according to claim 1, wherein the plurality of ultrasonic transducers of each respective circular ultrasonic transducer field are arranged on the lateral surface, and wherein each ultrasonic transducer has a main radiation direction into the measurement volume.

5. The device according to claim 1, wherein the plurality of circular ultrasonic transducer fields are arranged side by side and respective adjacent circular ultrasonic transducer fields are in contact.

6. The device according to claim 1, wherein the plurality of transducer fields are geometrically identical to each other.

7. The device according to claim 3, wherein the lateral surface is formed by a hemisphere or a half-ellipsoid.

8. The device according to claim 1, wherein each of the plurality of ultrasonic transducers of each respective circular ultrasonic transducer field has an out-coupling layer pointing towards the measurement volume.

9. The device according to claim 1, wherein the plurality of ultrasonic transducers of each of the plurality of ultrasonic transducer fields are arranged in an aperiodically random uniform distribution additionally due to distances between adjacent ultrasonic transducers being uniformly distributed in a value interval between the maximum distance and the minimum distance.

10. The device according to claim 1, wherein each of the plurality of circular ultrasonic transducer fields is in direct contact with the ultrasonic coupling medium over a respective circular area, and
wherein the plurality of ultrasonic transducers of each respective circular ultrasonic transducer fields is arranged in the aperiodically random uniform distribution over an entire interior of the respective circular area.

* * * * *